US007966062B2

(12) United States Patent
MacAdam

(10) Patent No.: US 7,966,062 B2
(45) Date of Patent: Jun. 21, 2011

(54) MULTI-COLOR OVERLAY SYSTEM FOR PROCESSING AND DISPLAYING ELECTROCARDIAC SIGNALS

(75) Inventor: David P. MacAdam, Millbury, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 1154 days.

(21) Appl. No.: 11/383,058

(22) Filed: May 12, 2006

(65) Prior Publication Data

US 2007/0010753 A1     Jan. 11, 2007

Related U.S. Application Data

(63) Continuation of application No. PCT/US2004/022221, filed on Jul. 9, 2004.

(60) Provisional application No. 60/487,897, filed on Jul. 11, 2003.

(51) Int. Cl.
*A61B 5/044*     (2006.01)
(52) U.S. Cl. ..................................................... 600/523
(58) Field of Classification Search ........... 600/523–525
See application file for complete search history.

(56) References Cited

U.S. PATENT DOCUMENTS

| 5,224,486 | A | * | 7/1993 | Lerman et al. | 600/509 |
|---|---|---|---|---|---|
| 5,284,152 | A | * | 2/1994 | Portnuff et al. | 600/525 |
| 5,540,232 | A | | 7/1996 | Laney et al. | |
| 6,236,883 | B1 | * | 5/2001 | Ciaccio et al. | 600/515 |
| 6,778,852 | B2 | | 8/2004 | Galen et al. | |
| 2002/0065459 | A1 | | 5/2002 | MacAdam et al. | |
| 2004/0243012 | A1 | * | 12/2004 | Ciaccio et al. | 600/509 |

FOREIGN PATENT DOCUMENTS

| WO | WO 01/80732 A2 | 11/2001 |
|---|---|---|
| WO | WO 01/91627 A2 | 12/2001 |
| WO | WO 02/058550 A2 | 8/2002 |
| WO | WO 03/022148 A1 | 3/2003 |

OTHER PUBLICATIONS

International Search Report for International Application No. PCT/US04/22221, Dated Apr. 1, 2005.

* cited by examiner

*Primary Examiner* — George R Evanisko
(74) *Attorney, Agent, or Firm* — Leason Ellis LLP

(57) ABSTRACT

In one aspect, a method for displaying closely proximate cardiac signals is provided and can include the steps of: (a) identifying one or more overlapping portions of a template signal and a data signal; (b) processing the overlapping portion so as to have a first color when displayed on a display; (c) processing the non-overlapping portion of the template signal to have a second color; (d) processing the non-overlapping portion of the data signal to have a third color; and (e) displaying the processed signals.

15 Claims, 10 Drawing Sheets

MULTI-COLOR OVERLAY SYSTEM FOR PROCESSING AND DISPLAYING ELECTROCARDIAC SIGNALS

CROSS REFERENCE TO PRIOR APPLICATION

This application is a continuation of PCT International Patent Application No. PCT/US200/022221, filed Jul. 9, 2004, which claims priority of U.S. Patent Application No. 60/487,897, filed Jul. 11, 2003, both of which are incorporated by reference herein. PCT International Application No. PCT/US200/022221 was published on Jan. 27, 2005 as Publication No. WO 2005/008418.

TECHNICAL FIELD

This invention relates to a system for processing and displaying electrical signals obtained from the heart and, more particularly, to a system that processes electrocardiac signals and displays the electrical signals using a multi-color scheme to assist the user in distinguishing between several signals and for indicating any overlapping portions thereof.

BACKGROUND

Certain cardiac arrhythmias are triggered or initiated from a site in the heart tissue other than the sinus node. These arrhythmias are classified as being "focal" in nature. Treatment of focal arrhythmias generally involves locating the arrhythmogenic site and ablating it. One method for regionally locating the focal site is the use of a diagnostic 12 Lead ECG. The 12 Lead can be used in conjunction with pacing via a roving intracardiac catheter to pace map the heart. The theoretical basis of this method assumes that the paced 12 lead ECG will appear identical to the non-paced ECG if the cycle length (i.e., paced heart rate) and pacing site matches the non-paced heart rate and focal site of origin.

One problem with this method (in current practice) is the subjectivity involved in visually comparing a non-paced 12 Lead ECG to a paced 12 Lead ECG. The same problem exists when viewing cardiac signals acquired from an intracardiac lead or from a data storage device.

A second problem is the time consuming nature of the procedure in which, typically, a spontaneous ectopic beat is recorded and printed on paper. A roving mapping catheter is positioned at a likely site of ectopy, pacing is initiated, a recording is made, a printout is generated and a visual comparison is made by aligning the printouts from the spontaneous and paced beats over one another. This process is repeated in an iterative manner until the physician determines that a good match between the spontaneous ectopic beat and the paced beat is found.

It will therefore be appreciated that it is a valuable tool for the physician to be able to easily compare components of the ECG (e.g., a beat of interest) with a template reference, such as a closely proximate cardiac signal. The comparison between a data signal (e.g., one cardiac signal) and a template signal (e.g., a closely proximate cardiac signal) can be done in a number of different ways, including the above method of aligning and overlaying printouts; however, these techniques all suffer from disadvantages that make it difficult for the physician to easily make a visual comparison between the printouts.

Moreover, when the cardiac signals are displayed on an electronic display (monitor) as compared to physically overlying printouts, they are typically displayed by placing one of the signals in a first display coordinate while the other signal is displayed in a second display coordinate that is above or below the first display coordinate. In other words, the signals are displayed independent of one another; however, this makes it difficult for the user to easily compare the two signals since the signals are not overlaid on one another and therefore, a visual comparison of different components of the ECG is complex and subject to human error.

As a result, systems have been developed that overlay one cardiac signal on top of the other cardiac signal on the electronic display so that the physician can compare the data signal (one cardiac signal) to the template signal (a template cardiac signal). However, the overlay of the two signals on the display signal creates another disadvantage in that the two signals are depicted on the display in the same color and, therefore, it can be difficult for the physician to distinguish one signal from the other signal. The physician is also interested in ascertaining where there is the best match between the two signals (i.e., the best overlap) and therefore, it is of interest for the physician to clearly see where there is a perfect overlap between the signals or where the two signals closely approximate one another. Unfortunately, the conventional technique of superimposing the signals does not always permit the physician to distinguish between the two signals, especially in the context of considering wave components of a cardiac signal.

The electrocardiogram typically includes an initial impulse, termed the P-wave, emanating from the atria, followed by what is termed the QRS complex, emanating from the ventricles, which is followed by a T-wave resulting from repolarization of the ventricles (FIG. 1). Thus, a heart beat begins with the P-wave and ends with the T-wave, and the next heart beat begins with another P-wave. The P-wave can be a valuable tool used by clinicians to diagnose the condition of the heart. Thus, clinicians will often monitor an electrocardiogram (ECG) of the heart to aid in the diagnosis of atrial and ventricular arrhythmias. This can be done in various ways, a most common technique being by monitoring the 12 Lead (surface) ECG in conjunction with observing the bioelectric activity recorded on intracardiac electrodes carried by a transthoracic catheter.

Accordingly, it will be apparent that there continues to be a need for a method that allows a clinician to pace map more effectively and more specifically, it is desired for a more efficient and effective technique for displaying a data signal (a cardiac signal of interest) over a template signal (e.g., another cardiac signal) and clearly indicating any overlap or close proximity between the two signals.

SUMMARY

The present invention, in certain aspects, provides a medical practitioner with a computerized method for objectively and efficiently performing real time pace mapping and other cardiac analyses, through the processing of incoming electrical signals which represent heart activity to display the electrical signals according to a multiple color scheme so as to permit the medical practitioner to easily distinguish one cardiac signal from the other and more importantly, to be able to discern where the two signals match one another or closely approximate one another.

In one aspect, a method for displaying closely proximate cardiac signals is provided and includes the steps of: (a) identifying one or more overlapping portions of a template signal and a data signal; (b) processing the overlapping portion so as to have a first color when displayed on a display; (c) processing the non-overlapping portion of the template signal to have a second color; (d) processing the non-overlapping portion of the data signal to have a third color; and (e) displaying the processed signals.

The present system and method aid the user in rapidly identifying overlapping portions of the two signals during electrophysiology procedures and avoids blending of the different signals at locations where they are closely proximate to each other or perfectly match each other during a template matching operation. This is a marked improvement over conventional systems and methods in which the two signals were displayed in an overlaid manner and it was very difficult for the practitioner to rapidly and easily determine areas in which the two signals overlapped or closely approximated one another.

Ordinarily, the colors mapped to the same coordinate on a monitor can be expected to blend in accordance with a conventional color superposition (based on color wheel principles). However, such blending typically does not possess the contrast on color representation to permit a clear differentiation of the two original colors. This is especially true when adjacent pixels display the individual colors. Thus, for example, yellow and red might blend to an orange, but the proximity of the yellow and red to the orange (on the color wheel) makes the orange difficult to discern and frustrates the operator's ability to gauge the quality of the signal overlap.

In accordance with a salient aspect of the invention, the assignment of a color to the overlapping or closely proximate signal portions is an arbitrary selection that is not dictated by a 50%/50% blend of the colors used for the data signal and the template signal. Preferably, the data signal and the template signals are two primary colors (red, yellow and blue) and the overlapping or closely proximate signal portions is the third primary color. When a secondary color (orange, violet, and green) is used in combination with two primary colors in the display, it is preferably not the secondary color that is bounded by the two primary colors.

The practitioner can be guided through visual aids such as bar graphs and overlaid cardiac signals of the quality of signal matches. These signal matches can assist in diagnosing a patient and in the effectiveness of an ongoing treatment, for example, an ablation procedure.

Other aspects, features and advantages of the invention can be more clearly understood from the following detailed description of exemplary embodiments and accompanying Drawing Figures.

DESCRIPTION OF THE DRAWINGS FIGURES

DETAILED DESCRIPTION OF THE PREFERRED EMBODIMENTS

To promote an understanding of the methods that can be practiced in accordance with preferred embodiments of the present invention, several pertinent aspects are discussed below under respective headings.

Template Matching/Pace Mapping

Any recorded ECG waveform can be used as a reference to compare to another recorded ECG waveform or to a real time ECG waveform. The comparison is performed in a two step process in which first a reference template is selected by the user to describe the beginning and end of an ECG waveform segment to be used as a comparison template. Next the user selects the region of data to be used for comparison—either from pre-recorded data or from the real time data stream. A suitably configured computer processor can find the best match against the reference template over the region specified, or in the case of real time analysis, find the best match updated over a defined period of time, for example every second. The criteria for "best match" utilizes a correlation coefficient calculation across all twelve leads of the ECG and finds the best alignment. This calculation may be preceded by a correlation assessment that is taken across fewer leads such as only one lead to generally align the reference template to the selected region of data that is of interest. A visual display showing the aligned reference beat (template) overlaid on the beat undergoing analysis give the user feedback as to the closeness of the match. A correlation coefficient calculated for each ECG lead gives a quantitative indicator of the match. A composite average is also calculated and is displayed in a unique color enhanced bar graph indicator which is especially useful when real time template matching is being performed. The composite average can be updated as a moving average over a preselected number of beats.

Template matching may be used to compare two spontaneous beats or it can be used to pace map, i.e., to compare a paced beat to a spontaneous beat. A Region of Interest (ROI) indictor can be manipulated by the user to exclude certain portions of the waveform from analysis. This is useful during pace mapping where pacing artifacts on the surface leads can be excluded from the region of analysis. The ROI indicator can also be used to specify a preference for T-wave or P-wave matching as they are oftentimes morphologically very similar.

T-Wave Subtraction

A method is provided whereby an ECG having an overlapping P and T wave is processed to remove the T-wave and thereby display the P-wave without any overlap, so that a clinician may observe the P-wave when performing a diagnosis of the heart.

Figure 1:
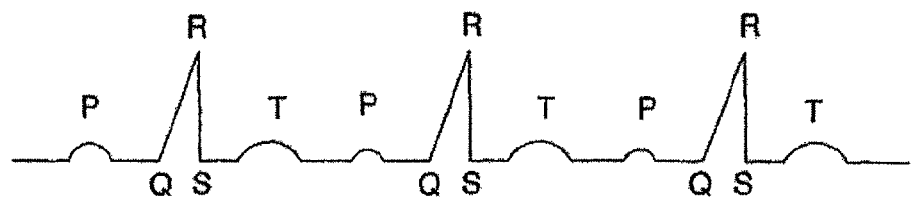
FIG. 1 is a schematic diagram of a normal heart beat.
Figure 2:
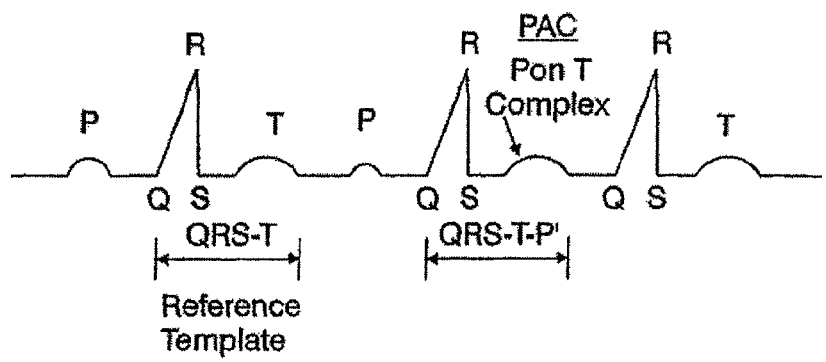
FIG. 2 is a schematic diagram of a pre-mature atrial contraction (PAC)

See FIG. 1 which describes a normal ECG over three beats in which distinctive P and T-waves can be identified. FIG. 2 shows a rhythm in which the P-wave from the third beat (P') arrives early and is obscured by the T-wave from the second beat. This results in what is termed a P on T complex, and is referred to as a QRS-T-P' in the figure.

In general, according to the method, the QRS-T segment of a beat that lacks a PAC is selected as a template. This template is subtracted from the QRS-T-P' signal in the PAC to be studied yielding the P-wave. The QRS-T signal used as the template may be from a single beat or it may be derived from an average of multiple beats. The QRS-T signal (or average) used as the template is selected so that the preceding QRS-QRS interval is equal (or nearly equal) to the QRS-QRS interval immediately preceding the QRS-T-P' signal to be studied. Preferably, the beat immediately preceding the PAC can be used for the selected QRS-T template as the cycle length and hemodynamic conditions of this beat are the closest to those of the succeeding beat that contains the PAC and P on T complex. (See FIGS. 2 and 3.)

The QRS complex is used as a means to synchronize and align the QRS-T template and the PAC beat for subtraction. The alignment is automated by the algorithm for the best match based on the composite correlation coefficient across the 12 Lead ECG. The practitioner has the option of shifting the template match left or right on a sample by sample basis with the resulting composite correlation coefficient updated at each new position. The practitioner also has the option of choosing the previous or following QRS-T segment as the reference template. The software will automatically locate the previous or following beat based on the current reference template and use the corresponding QRS-T segment of that beat as the new reference template in the calculation of derived P-waves.

Different display views showing the derived P-wave, alone, or overlaid with the original PAC beat or reference template are available as an aid to the practitioner.

P-waves that have been derived using the T-wave subtraction method can be signal processed further to remove unwanted artifacts caused by respiration or noise.

3. Template Matching of Derived P-Waves

Once one has a derived P-wave identified from the tachycardia or premature atrial beat (PAC), one can compare this derived P-wave with a previously captured reference template.

3a. More specifically, one or more spontaneous P-waves may be identified using the subtraction method described above and compared with one another using a correlation waveform analysis. This can be used to determine if the spontaneous P-waves have the same focal origin. This can be done in real time or in review from recorded data.

3b. In addition, one or more derived spontaneous P-waves may be identified and compared to a library of P-waves of known focal origin to predict the most likely site of origin.

3c. In addition, once a derived spontaneous P-wave is identified by the T-wave Subtraction method as described above then the practitioner can begin atrial pace mapping following the Template Matching/Pace Mapping method also described above. The roving pace mapping catheter is maneuvered within the atria (or adjacent vessels such as the pulmonary veins) until the derived paced P-wave is nearly identical to the derived spontaneous P-wave. This comparison of derived P-waves may be done on pre-recorded data or in real time.

More generally, two or more waveforms X, Y, . . . , may form a composite waveform that due to timing and amplitude relationships causes the individual waveforms to be obscured or hidden. The composite waveform includes a synchronous subcomponent overlapping a non-synchronous subcomponent. If a singular, unadulterated sub-component waveform (e.g. X or Y) can be identified, and if it has similar timing characteristics that allow it to be synchronized with the composite waveform (i.e., this identified subcomponent is the synchronous subcomponent), then it can be subtracted from the composite waveform to derive the other sub-component waveform(s) (i.e., the non-synchronous subcomponent(s)). Sub-component waveforms, either derived, native state, or pace induced, can be quantitatively compared to one another using correlation analysis. This analysis may be done retrospectively or in real time. One of skill in the art will appreciate that a number of algorithms can be used to compare waveform shape, including, but not limited to bin area methods and integrals; any of these methods can assist in the goals of aligning synchronous components of composite waveforms and/or comparing the derived results.

A method in accordance with this more general teaching proceeds generally as outlined above. Specifically, this method proceeds in substantially the same manner as when deriving a p-wave from a PAC beat, but more generally includes the selecting the synchronous subcomponent of the heartbeat signal, permitting a user to mark a begin point and an end point of the selected synchronous subcomponent, defining a reference template as being a waveform segment between the marked begin and end points of the selected synchronous subcomponent, acquiring the composite waveform at the signal processing unit from multiple leads, and processing the composite waveform beat so as to derive the non-synchronous subcomponent.

Figure 4:
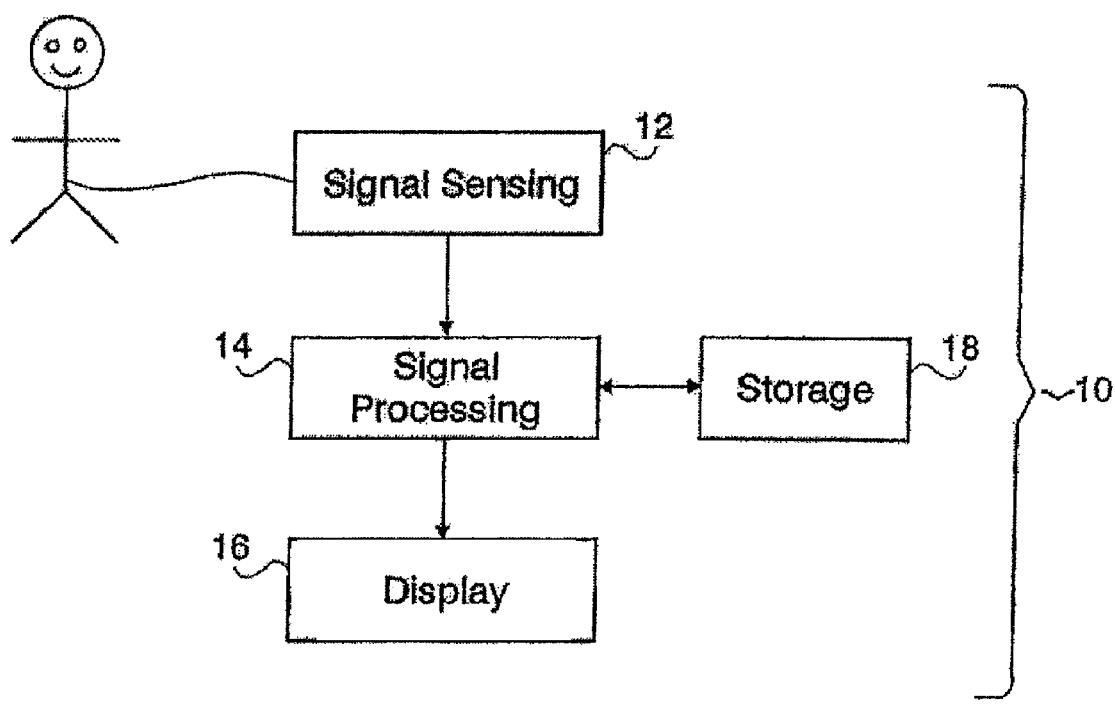
FIG. 4 is a block diagram of a system programmed to practice a method in accordance with a preferred embodiment.

Referring now to the drawings, and particularly to FIG. 4, there is shown a system 10 for receiving and processing electrical signals according to one illustrative embodiment of the present invention. In one illustrative embodiment, the system 10 includes a signal sensing unit 12, which may take different forms, such as a standard 12 lead ECG, intracardiac lead, or combination thereof. The signal sensing unit is electrically connected to a signal processing device 14, which receives the sensed signals from the unit 12 and processes the signals, as is described in more detail below. The signal processing device ("signal processor" or "processor") 14 is preferably connected to a suitable display 16, which will present the processed signals to a clinician or other interested person. Information can be stored and recalled from a storage device 18. Preferably the signal processing device 14 and display 16 comprise the EP LabSystem (trademark) of C.R. Bard, Inc., Murray Hill, N.J., or the like. The EP LabSystem (trademark) supports a variety of data gathering and processing functions that are standard in electrophysiology procedures, and can have its hardware (namely, processor 14) configured to implement the subtraction and derivation methods set forth above, for example, through software (e.g., modules, procedures, functions, or objects) or firmware. The processor 14 communicates with a memory or storage 18 which configures the processor to implement the subtraction and derivation methods above (as well as the integral techniques described below).

In one illustrative embodiment, the special features of the system of the present invention are implemented, in part, by a processor using program information stored in a memory of the signal processing device 14. The processor 14 can access one or more files, as necessary, to implement the required functions, as described in greater detail in connection with FIG. 5 and FIG. 6.

Figure 5:
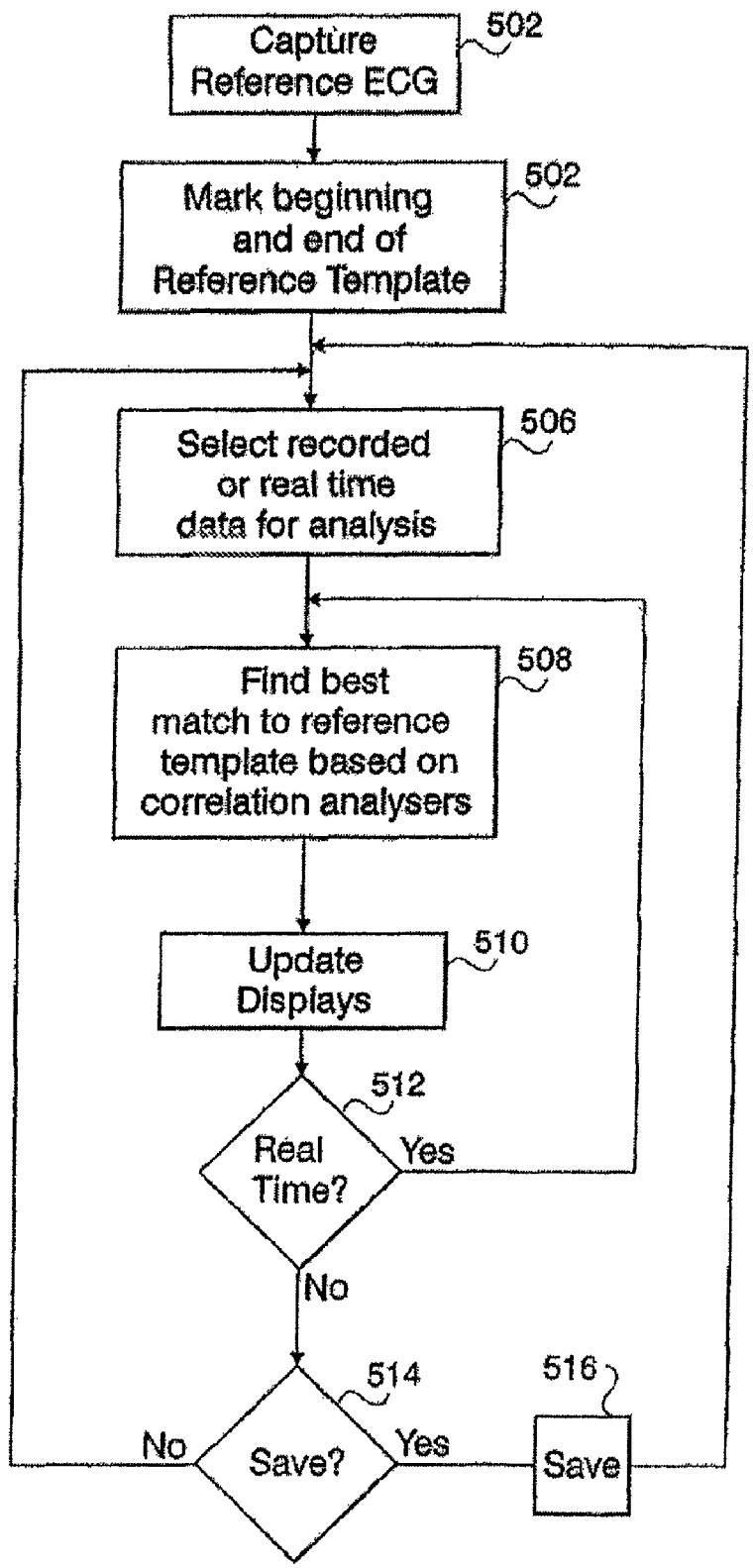
FIG. 5 is a flow diagram showing the process for template matching in accordance with the preferred embodiment.

Referring now to FIG. 5, the operation of the signal processing device 14 of the present invention is described in conjunction with the above structural description of the system 10. As illustrated in FIG. 5, the process begins when a clinician desires to create a reference template, and this occurs by capturing a reference ECG signal, as indicated at step 502. Preferably, the reference ECG signal is captured using a standard 12 lead device and/or one or more intracardiac leads. As explained above in connection with FIG. 2, the QRS-T signal components of a beat which does not exhibit P-on T-wave are selected as a template and it is this set of electrocardiac signal components that is captured at step 502. Such a beat can be captured in sinus rhythm or during a focal arrhythmia such as a tachycardia. Furthermore, it is contemplated that the reference template results from signals captured either at the surface, from intracardiac leads that can be placed in a variety of locations within the heart, or a combination of signals from surface and intracardiac leads. The QRS-T signal that is used as the template can be captured from a single heartbeat or may be a signal derived from an average of multiple heart beats.

At step 504, beginning and end points of the reference template are marked by the clinician using an interface to the signal processing unit 14. The marked points define the segment of the ECG waveform to be used as a comparison template.

At step 506, the clinician selects whether recorded or real-time data is to be used in the template matching analysis. (This step can be performed at any time prior to the waveform matching analysis at step 508, for example, prior to performing steps 502 and 504.) If recorded data is to be used in the template matching analysis, then a specified region of pre-recorded data is provided to the signal processing unit for comparison to the reference template. On the other hand, if real-time data is to be used in the template matching analysis, a stream of data from ECG leads is provided to the signal processing unit 14 over a defined period of time for comparison to the reference template.

At step 508, the signal processor 14 finds a "best match," in other words, a best alignment between the selected region or time period and the reference template.

At step 510, the display 16 is updated to indicate to the clinician (or other persons) the result of the template match. The results can be shown qualitatively as superimposed ECG waveform signals, namely, the reference beat (template) overlaid upon the beat under analysis to show the degree of alignment therebetween, or quantitatively as a correlation coefficient calculated for each ECG lead. Preferably, a composite average is also calculated and displayed. This is illustrated in the computer display shown in FIG. 8.

At step 512, a test is made to determine whether the user had selected real-time processing at step 506. If so, then the flow loops back to step 508 to again perform the template matching analysis and to update the display accordingly. Otherwise, if previously recorded segments are being analyzed, the user is given the option to save the analysis (as tested at step 514), and the correlation analysis is saved, as indicated at step 516. Real-time analyses can also be saved if desired.

Figure 6:
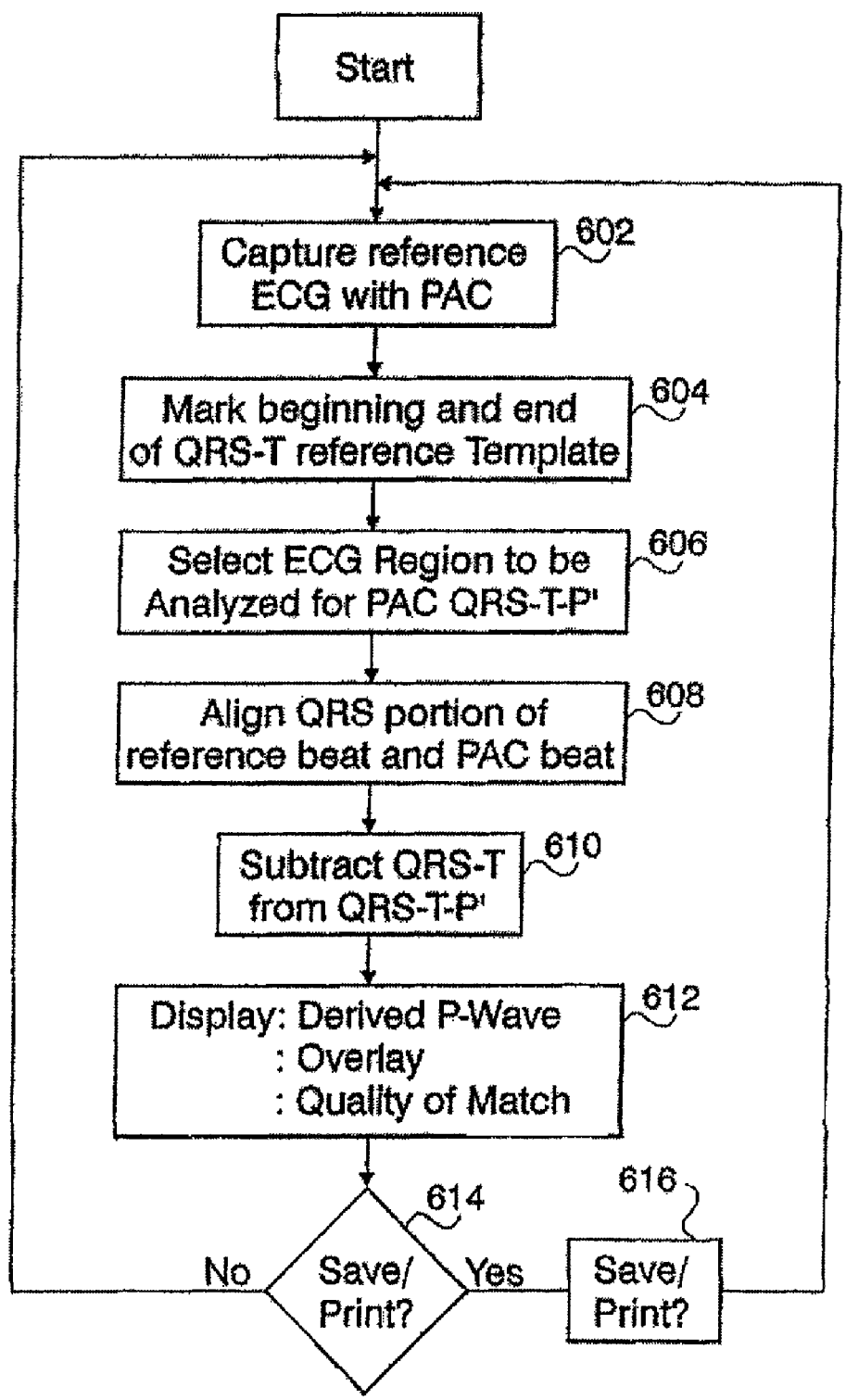
FIG. 6 is a flow diagram showing the process for T-wave Subtraction in accordance with the preferred embodiment.

Referring now to FIG. 6, the operation of the signal processing device 14 of the present invention is described in conjunction with the above structural description of the system 10. As illustrated in FIG. 6, the process begins at step 602 when a clinician captures a PAC and desires to subtract a QRS-T reference template from the PAC. The QRS-T reference template is marked by the clinician at step 604 (as described above) and a region encompassing the PAC is selected by the clinician at step 606 for analysis. The QRS portion of the reference template is aligned for best fit with the QRS complex immediately preceding the PAC at step 608. When the best fit is found, the processor 14 subtracts the QRS-T reference template from the QRS-T-P' segment of the PAC at step 610.

Figure 7:
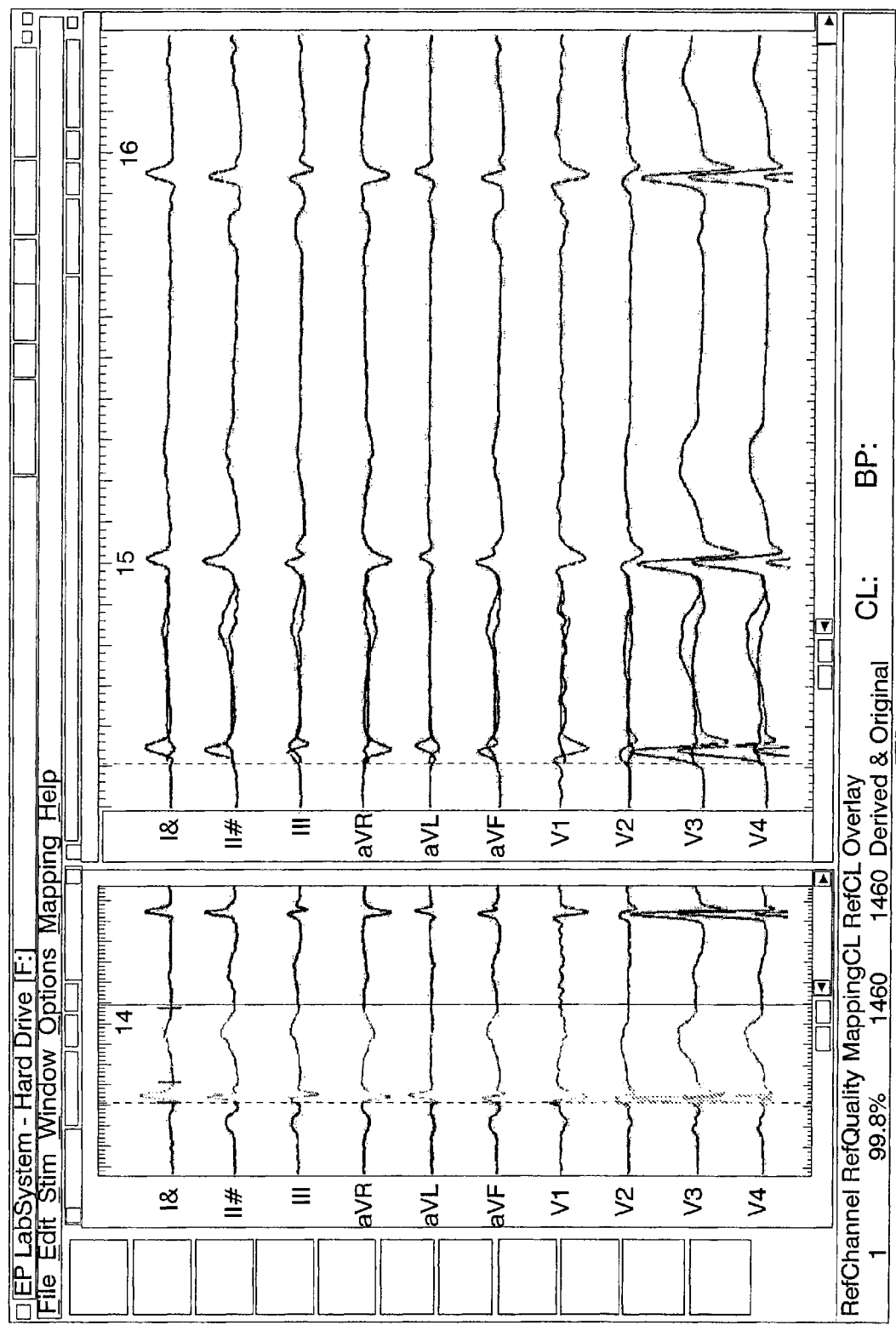
FIG. 7 is a representative computer display interface for T-wave subtraction that can be displayed to an operator.

The difference is the derived P-wave which is output to the display 16 at step 612. This is illustrated in the computer display shown in FIG. 7, in which the leftmost window displays the selected QRS-T reference template between two vertical lines (one dashed line prior to the 14 second mark at the top (highlighted by an arrow), and a second solid line just after the 14 second mark). The rightmost window shows the original PAC waveform with the derived P-wave overlaid on top of the portion of the ECG which occurs in the first 15 seconds. The overlaid and derived P-wave appears as a second graph superimposed over the ECG signals. Visual aids can be provided to automatically align and overlay waveforms for visual comparison on a computer display or a printout.

Figure 8:
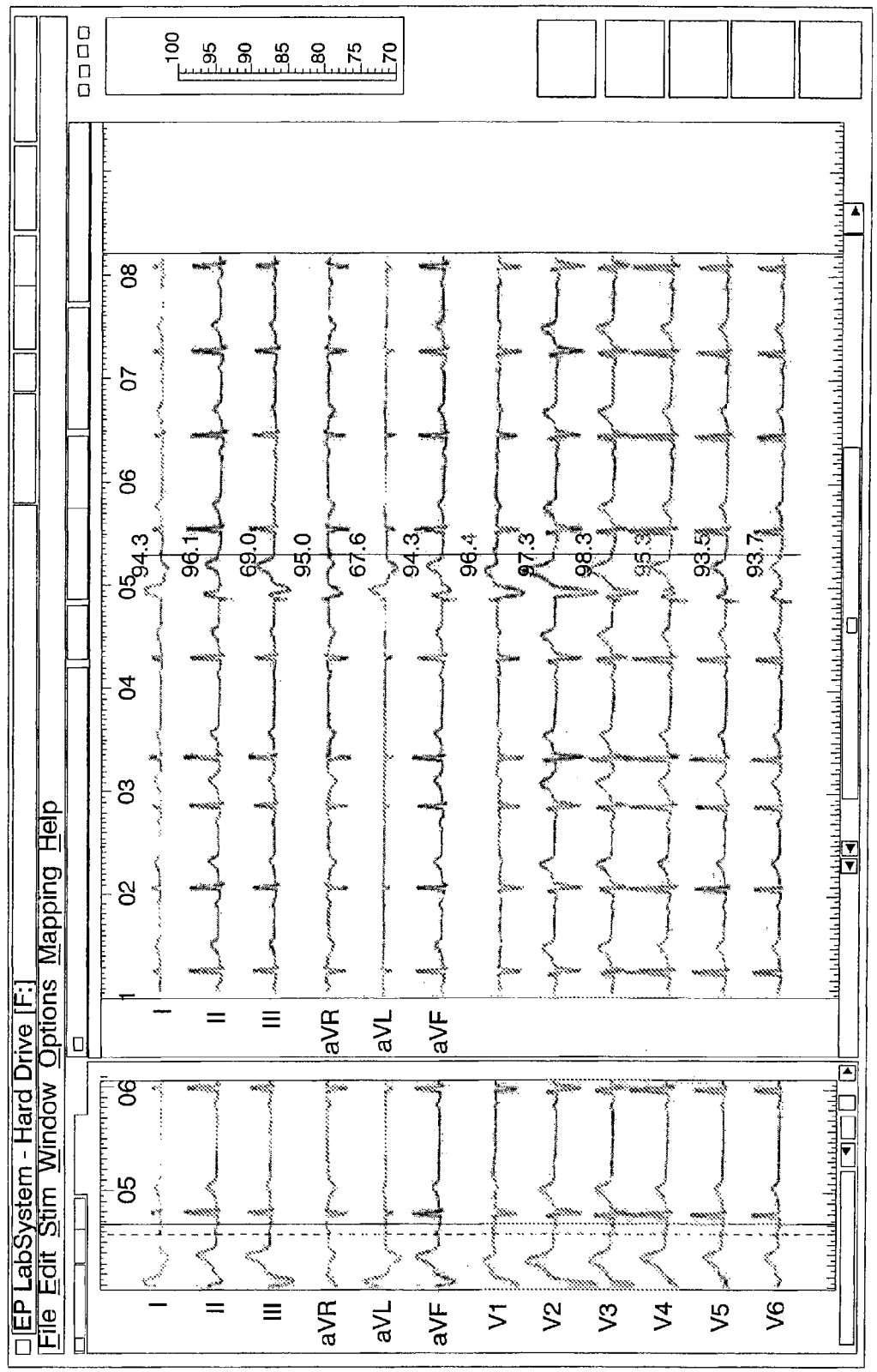
FIG. 8 is a representative computer display interface for template matching that can be displayed to an operator.

FIG. 8 illustrates an exemplary display for template matching (without subtraction) that can be displayed to an operator. The leftmost window displays markers which signify the presence and use of the reference template; the reference template beginning at the leftmost vertical line (highlighted by the arrow) and ends at the second vertical line. In this example, the reference template marks the start and finish of a P-wave; however, any waveform segment can be used if the region of interest has been marked for use as a template. The larger display window to the right shows the correlation value for each channel of the 12 Lead ECG as compared to the reference template. The bar graph at the far right is inactive in this example because the analysis region is taken from recorded data rather than real-time data gathered during a medical procedure.

The data can be saved, printed or both, if desired, in response to a user input to do so, as tested at step 614 and implemented at step 616.

From the foregoing, it will be apparent to those skilled in the art that the present invention provides a method for reliably and efficiently recovering a P-wave from a waveform that has overlapping P- and T-waves. Furthermore, the template matching capabilities of the invention provide the added benefit of quickly and objectively comparing ECG waveform components, in their native or derived state. It should also be understood that the correlation, subtraction and derivation methods described herein apply to data that can be acquired from conventional 12 lead surface ECG signals as well as intracardiac signals or combinations of both surface and intracardiac signals.

Two waveforms can have a high correlation to each other but still be poorly matched in absolute terms due to amplitude variation and drift caused by the effects of respiration. This can be a problem when two waveforms are aligned and then subtracted, one from the other. It is for this reason that immediately adjacent beats are usually desirable as the reference (QRS-T) and PAC (QRS-T-P'). This is not always possible and is not practical when performing real time pace mapping.

Figure 3:
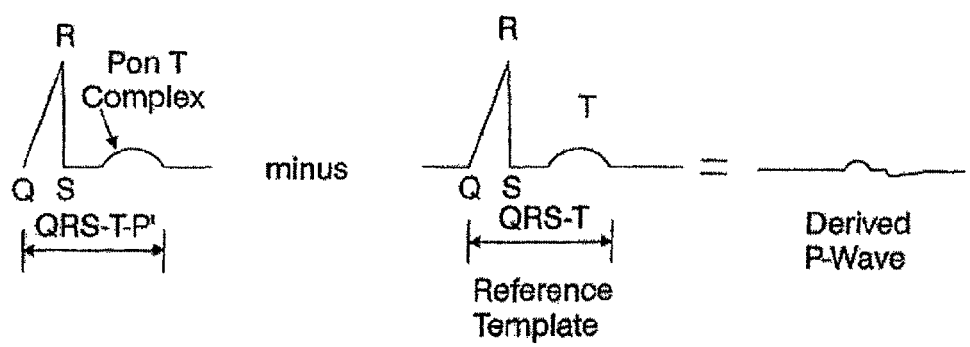
FIG. 3 is a schematic diagram of the T-Wave subtraction.
Figure 9:
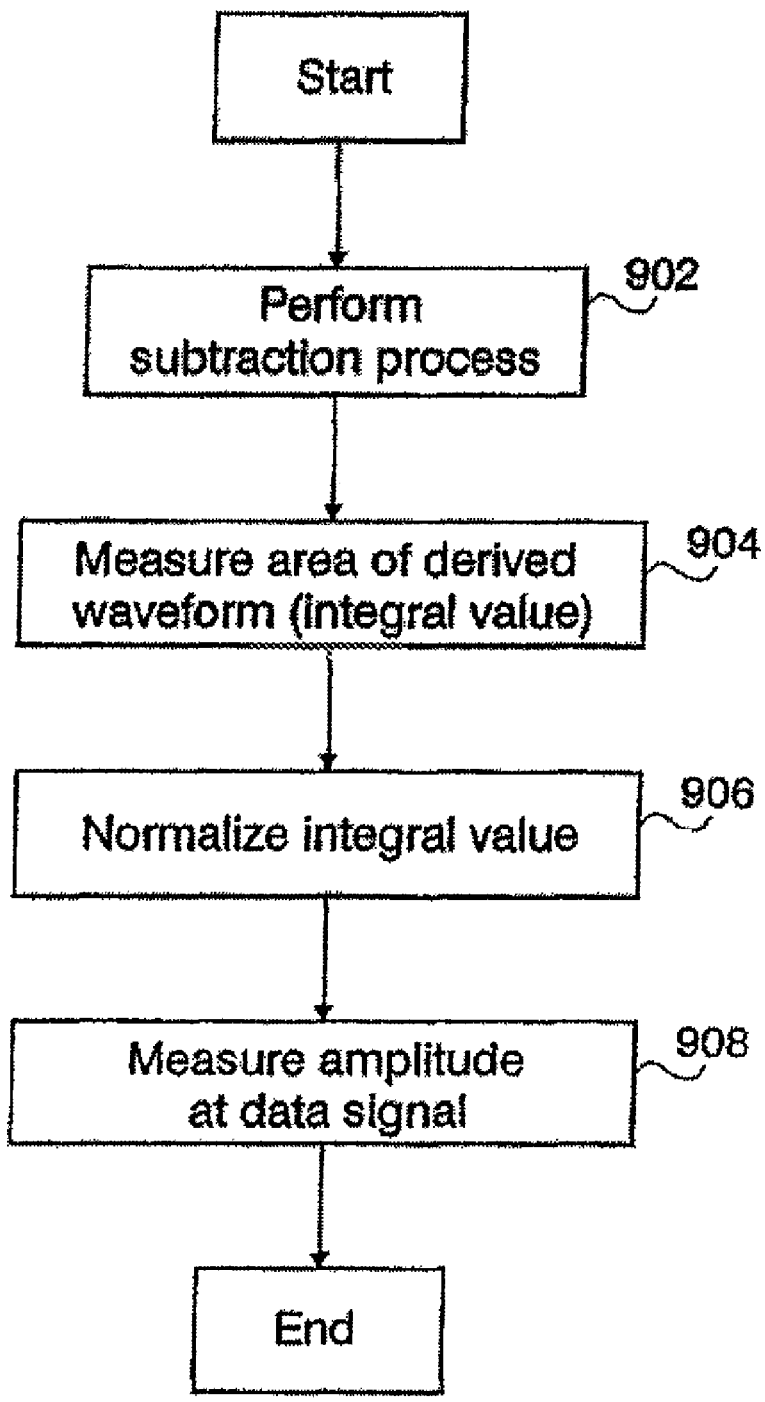
FIG. 9 illustrates a methodology for determining the integrals of a section of the QRS_T segment after the subtraction process.
Figure 10:
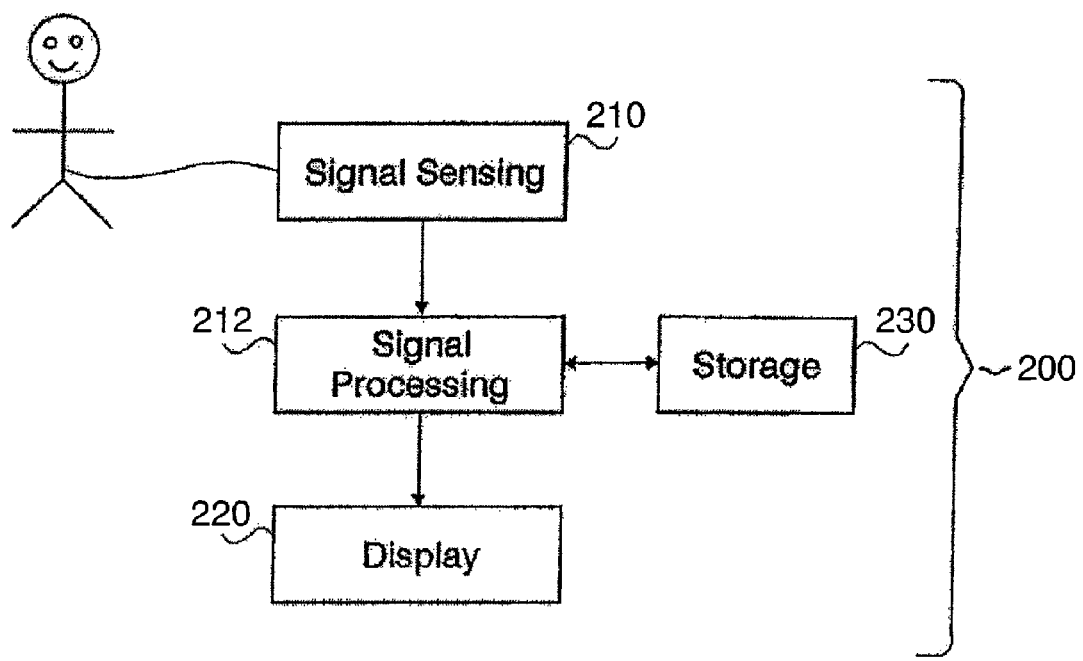
FIG. 10 is a block diagram of a system programmed to practice a method of displaying the electrical signals according to a multi-color scheme.

A methodology for monitoring the quality of the T-Wave subtraction is now described with reference to FIG. 9. At step 902, a subtraction process (as illustrated in FIGS. 3 and 6 and described above) is performed to subtract a QRS-T template from a PAC (QRS-T-P') and thereby derive a waveform. The method of FIG. 9 proceeds by then providing integral calculations that enable a number of measurements of interest to practitioners, including, but not limited to: measures of QRS residue and the quality of the T-wave subtraction process; measures of the baseline drift, if any; and optimization of the selection of templates to be used in the subtraction process.

At step 904, the area of a derived waveform is measured. At step 906, the integral value is divided by the length of the derived waveform to normalize its value. In addition, at step 908, the amplitude of the normalized integral value is measured and displayed as a voltage at the ECG channel's input. This voltage value is termed the QRS residue.

As described earlier, correlation analysis is used to align the QRS segment of a reference ECG template with the QRS segment of a PAC beat. Thus a further improvement may use the correlation coefficient in conjunction with the so-called QRS residue of the derived waveform to give an indication of the quality if the match between two beats chosen for subtraction. Together, they provide an indicator of the alignment or synchronization quality between the template QRS and the PAC QRS. For a perfect alignment and good subtraction results, the derived QRS segment should be flat indicating a high correlation to the template and the QRS residue should be very small indicating a small difference in absolute amplitudes (including drift).

Referring now to FIGS. 10-13 in which a template matching process and display according to another embodiment is illustrated. A system 200 is provided and includes a signal sensing unit 210, which can take different forms, such as a standard 12 lead ECG, intracardiac lead, or combination thereof. The signal sensing unit 210 is electrically connected to a signal processing device 212, which receives the sensed signals from the unit 210 and processes the signals as is described in greater detail below. The signal processing device ("signal processor" or "processor") 212 is preferably connected to a suitable display 220 which presents the processed signals in multi-color format to a clinician or other interested person to assist in distinguishing the signals from one another and indicating portions of the signals that match one another (overlap) or closely approximate one another as will be described below. Information can be stored and recalled from a storage device 230.

The signal processing device 212 and display 220 are units that perform the intended functions and are designed for the intended applications described herein. For example, the processing device 212 and display 220 can be the EP LabSystem (trademark) or a modified version thereof commercially available from C.R. Bard, Inc., Murray Hill, N.J. or it can be another device from another manufacturer. The signal processing device 212 supports a variety of data gathering and processing functions that are standard in electrophysiology procedures and can have its hardware (namely, processor 212) configured to implement the processing operations described herein through software (e.g., modules, procedures, functions, or objects) or firmware. The processor 212 communicates with the memory or storage 230 which configured the processor 212 to implement the integral techniques described herein as well as the other processing methods.

In one embodiment, the feature of the system 200 are implemented, in part, by a processor using program information stored in a memory of the signal processing device 212. The processor 212 can access one or more files, as necessary, to implement the required functions as described herein.

Figure 11:
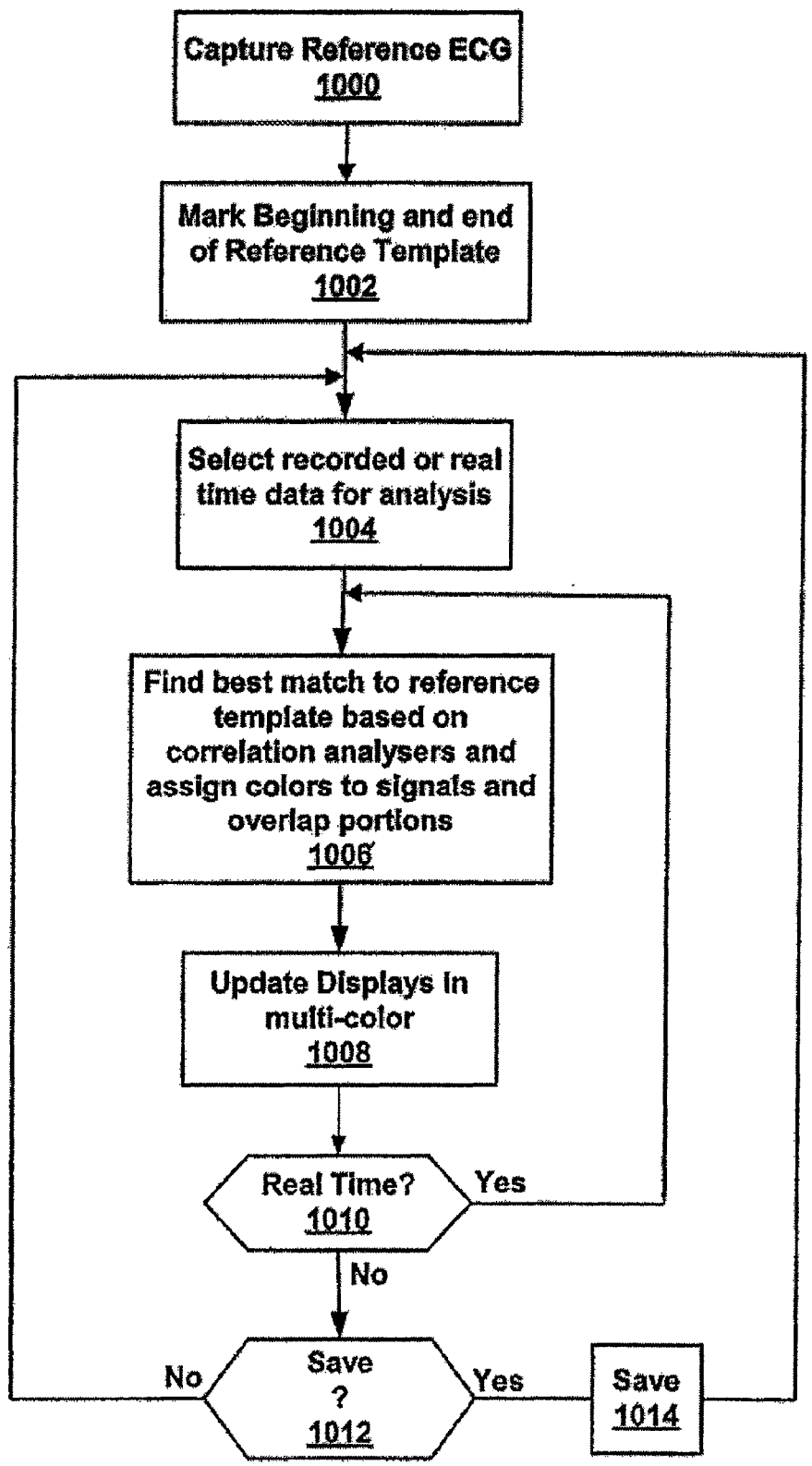
FIG. 11 is a flow diagram showing the process for template matching in accordance with one preferred embodiment.
Figure 12:
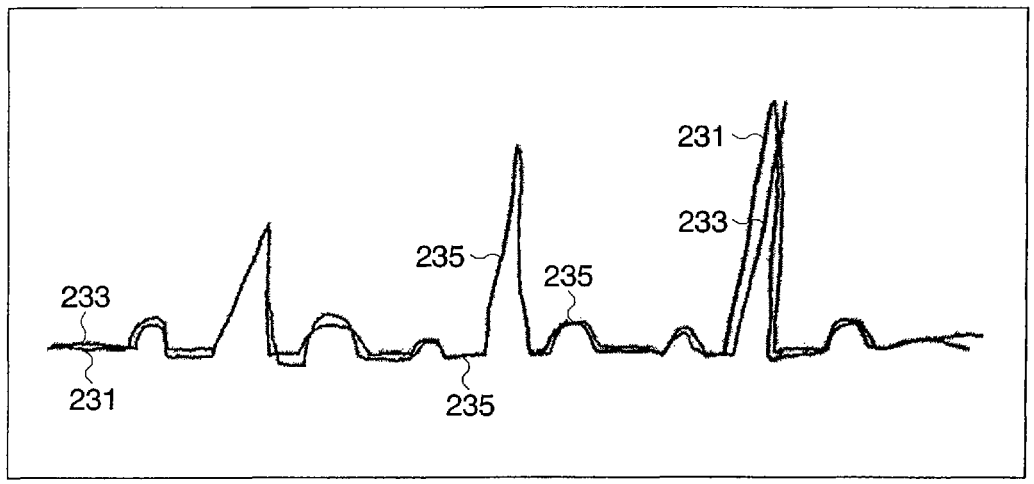
FIG. 12 is a representative display for a multi-color template matching that can be displayed to an operator.
Figure 13:
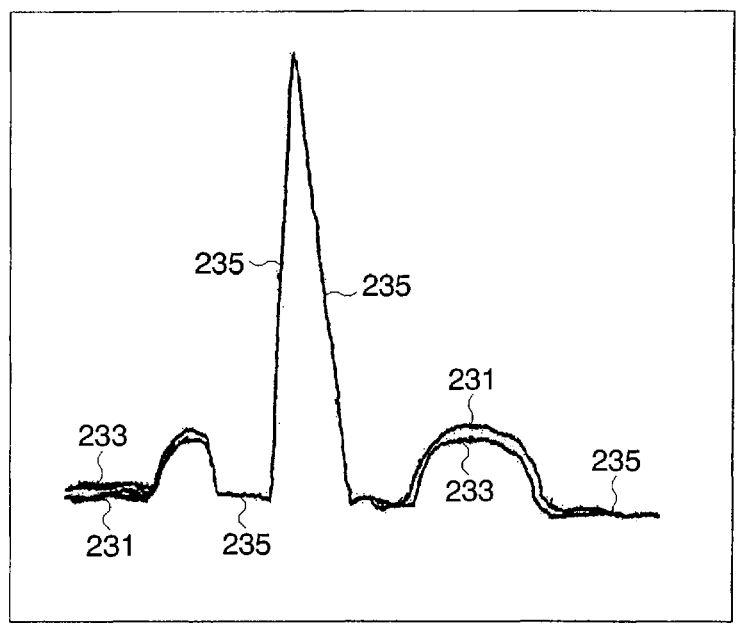
FIG. 13 is an enlarged section of the display of FIG. 12 illustrating that a three color overlay nature of one exemplary system.

With reference to FIGS. 11-13, the operation of the signal processing device 212 is described in conjunction with the above structural description of the system 200. As illustrated in FIG. 11, the process begins when a clinician desires to create a reference template and this occurs by capturing a reference ECG signal as indicated at step 1000. Preferably, the reference ECG signal is captured using a standard 12 lead device and/or one or more intracardiac leads. The reference template (reference ECG signal) should be a cardiac signal in which the QRS-T signal components of a beat do not exhibit P- on T-wave and thus, it is this set of electrocardiac signal components that is captured at step 1000. Such a beat can be captured in sinus rhythm or during a focal arrhythmia such as a tachycardia. Furthermore, it is contemplated that the reference template results from signals captured either at the surface, from intracardiac leafs that can be placed in a variety of locations within the heart, or a combination of signals from surface and intracardiac leads. The QRS-T signal that is used as a template can be captured from a single heartbeat or can be a signal derived from an average of multiple heartbeats. It will also be appreciated that while the reference template signal is described above in terms of a QRS-T signal, the operator can define it otherwise by simply inputting such instruction to the processor 212 (e.g., by marking a set of electrocardiac signal components as the template signal). The template is assigned a first color by the signal processor 212.

At step 1002, beginning and end points of the reference template can be marked by the clinician using an interface to the signal processing unit 212. The marked points define the segment of the ECG waveform to be used as a comparison template.

At step 1004, the clinician selects whether recorded or real-time data is to be used in the template matching analysis. (This step can be performed at any time prior to the waveform matching analysis at step 1006, for example, prior to performing steps 1000 and 1002). If recorded data is to be used in the template matching analysis, then a specified region of pre-recorded data is provided to the signal processing unit 212 for comparison to the reference template. On the other hand, if real-time data is to be used in the template matching analysis, a stream of data from ECG leads is provided to the signal processing unit 212 over a defined period of time for comparison to the reference template.

In accordance with this embodiment, the signal processor 212 assigns a second color to the data signal that is different from the first color of the template signal. In other words, the signal processor 212 assigns a color to the data signal that is easily distinguishable from the color that is assigned to the template signal so that when the template signal is superimposed on (laid over) the data signal, the two signals can easily be distinguished by the clinician (and others) since the two signals are visually displayed in two different distinguishable colors.

At step 1006, the signal processor 212 finds a "best match", in other words, a best alignment between the selected region or time period and the reference template. For purpose of simplicity, step 1006 is also shown as being the step where the processor 212 assigns different colors to each of the two signals and a further color to the overlapping portions thereof. It should be understood that color assignment needs to precede the display of the individual and the overlapping or closely proximate signals.

At step 1008, the display 230 is updated to indicate to the clinician (or other persons) the result of the template match using the above described multi-color scheme. The results can be shown qualitatively as superimposed ECG waveform signals, namely, the reference beat (template signal) overlaid upon the beat under analysis (data signal) to show the degree of alignment therebetween, or quantitatively as a correlation coefficient calculated for each ECG signal. Preferably, a composite average is also calculated and displayed.

A test at step 1010 determines whether the data signal is provided in real-time and, if so, the process at steps 1006 and 1008 is repeated. Otherwise, the preferred process continues to prompt the user to save the data at step 1012, which is saved at step 1014 or not.

In accordance with this embodiment, the system 200 can be referred to as a multi-color overlay system on the basis that the two compared signals (template and data) are assigned and displayed in different distinguishable colors on the display 230 when overlaid and a third color is used to show where there is overlap or matching of the two signals within some threshold range. In FIGS. 12 and 13, the template signal in the first color is illustrated by the legend 231, the data signal in the second color is illustrated by the legend 233 and the overlapping or matching areas of the two waveforms when superimposed are illustrated by the legend 235 for purpose of illustration only since it will be appreciated that the different waveforms and the overlapping thereof are readily discernable when a multi-color display 230 is used.

In other words, the signal processing device 212 operates by first capturing and identifying a template signal and assigning this template signal a first color when the template signal is displayed on the display 230. Similarly, the data signal is identified and assigned a second color and then the signal processing device 212 overlays the template signal on top of the data signal to show the degree of alignment therebetween. The use of two colors to distinguish the two signals is an advancement over conventional data processing and display techniques in which the two signals were displayed in the same color and, therefore, the two signals easily blended together and this required great care and time by the clinician to closely observe the two signals. The situation is further complicated when the two signals match one another in one or more regions or areas and accordingly, in these areas, the signals typically blend with each another and therefore it can be difficult to determine whether the two signals are in fact overlapped or merely separated by a small distance. While, it may be possible for the overlapped region(s) to be indicated using some other indicator indicia, such as a dashed line or dotted line, compared to the solid lines of the non-overlapping portions of the signals, this distinguishing approach can still not be adequate enough for the clinician to quickly determine whether and where the signals overlap. In other words, because when the two signals are displayed in the same color and the overlapping indicia is also displayed in the same color, it can be difficult for the clinician to quickly and accurately determine overlapping regions.

The present system 200 overcomes all these disadvantages associated with the conventional systems since multiple colors are used to distinguish the template and data signals themselves as well as the use of a different distinguishable color to indicate where the two signals overlap one another (e.g., perfect match) or are within some programmed threshold range from one another. Since three colors are used to indicate different relationships between the two signals, the clinician can easily and quickly glance at the display 230 and determine the degree of overlap or match between the template and data signals as well as the precise location where the two signals overlap since this region is illustration by having its own color as illustrated in FIGS. 12-13.

Preferably, the template signal and the data signal are closely proximate to one another in time and location along the ECG and it will be appreciated that the template signal and the data signal can even be partially overlapping as in the case of a PAC as described hereinbefore. For example, the data processing device 212 can be configured such that the relationship between the template signal and the data signal is that the template signal is the cardiac signal (QRS-T signal) occurring just prior to the beat under analysis (data signal) or vice versa, namely, the data signal can be the signal that is immediately prior to the template signal. Any number of other arrangements can be possible in that the data processing device 212 can be configured so that the relationship between the template and data signals is inputted therein and is readily changeable. For example, the data processing device 212 can be programmed so that the data signal is the second cardiac signal following the template signal or vice versa. In order to provide the clinician with helpful information, it is preferred that the template and data signals be closely proximate one another so that the clinician can compare these closely proximate signals in an overlaid manner to understand the behavior of the heart by observing close in time heart beats.

The degree of alignment between the template signal waveform and the data signal waveform which is required before the signal processing device 212 identifies it as overlapping and assigns the third color to this area is programmable by the clinician, etc. More specifically, the signal processing device 212 can be programmed so that not only perfectly matched portions of the template signal waveform and the data signal waveform are indicated in the third color but also portions where the degree of alignment between the two waveforms exceeds some threshold value are also indicated in the third color as being generally overlapping with one another. For example, the signal processing device 212 can be programmed so that the third color is used to indicate portions where the percent correlation between the template signal waveform and the data signal waveform exceeds a predetermined threshold value, such as 95% (or some other inputted value, such as greater than 90%, etc.). In other words, there does not have to be a perfect match (100% correlation) for the third color to be used to indicate and highlight a waveform portion for viewing by the clinician.

The present system 200 thus aids the user in rapidly identifying overlapping portions of the two signals during electrophysiology procedures and avoids confusing the different signals where they are closely approximate each other during template matching.

It should be understood that the description "first color", "second color" and "third color" can be used interchangeably for the data signal, the template signal and overlapping or closely proximate signal portions.

Ordinarily, the colors mapped to the same coordinate on a monitor can be expected to blend in accordance with a conventional color superposition (based on color wheel principles). However, such blending typically does not possess the contrast on color representation to permit a clear differentiation of the two original colors. This is especially true when adjacent pixels display the individual colors. Thus, for example, yellow and red might blend to an orange, but the proximity of the yellow and red to the orange (on the color wheel) makes the orange difficult to discern and frustrates the operator's ability to gauge the quality of the signal overlap.

In accordance with a salient aspect of the invention, the assignment of a color to the overlapping or closely proximate signal portions is an arbitrary selection that is not dictated by a 50%/50% blend of the colors used for the data signal and the template signal. Preferably, the data signal and the template signals are two primary colors and the overlapping or closely proximate signal portions is the third primary color. As one will appreciate a color wheel describes the relationships between colors. It is laid out so that any two primary colors (red, yellow, and blue) are separated by secondary colors (orange, violet, and green). Each secondary color is bounded by two primary colors and it is these components that one would mix to get that secondary color. In addition, color complements are color opposites and these colors contrast each other in the most extreme way. For example, blue and orange are color complements as well as violet and yellow as well as red and green.

As previously mentioned, in one embodiment, the two signals and the overlapping or closely proximate portions are indicated using the three primary colors. In another embodiment, two of the signals or the overlapping or closely proximate portions are primary colors and the third is a color which is a color complement to one of the primary colors used for the two signals. For example, if red and blue are the primary colors used for the two signals than the overlapping or closely proximate portions can be shown in either orange or green (color complements of the blue and red primary colors). Preferably, the overlapping or closely proximate portions are not indicated by a color which is a secondary color that is bounded by the two primary colors used to display the two signals since this leads to the above described blending problem.

Alternatively, the two signals and the overlapping or closely proximate portions can be represented by the three secondary colors.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A method for displaying closely proximate cardiac signals comprising the steps of:
    identifying one or more overlapping portions of a template signal and a data signal, wherein the template signal and the data signal each comprise a segment of a electrocardiogram (ECG) waveform signal;
    processing the overlapping portion so as to have a first color when displayed on a display;
    processing the non-overlapping portion of the template signal to have a second color;
    processing the non-overlapping portion of the data signal to have a third color, wherein the first color is different than the second and third colors; and
    displaying the processed signals in the first, second and third colors to show the degree of alignment therebetween,
    wherein the identifying step identifies the overlapping portions as including (a) perfect matches between the template signal and the data signal, and (b) not perfect matches of closely-approximating, additional portions in which a degree of alignment between the template signal and the data signal exceeds a predetermined threshold value.

2. The method of claim 1, including the additional step of deriving the data signal from an average of segments of ECG waveform signals from multiple beats of a heart.

3. The method of claim 1, wherein the overlapping portion is defined as portions of the template signal and data signal that perfectly match one another.

4. The method of claim 1, wherein the threshold value is greater than 95% correlation.

5. The method of claim 1, wherein the first, second and third colors are readily distinguishable from one another.

6. The method of claim 1, including the additional steps of capturing ECG waveform signals and selecting first and second ECG waveform signals from respective first and second heart beats that occur immediately after one another, wherein the first ECG waveform signal represents the data signal and the second ECG waveform signal represents the template signal.

7. The method of claim 1, further including the steps of:
    calculating a quantitative indicator of a correlation coefficient calculation that is used to identify a best fit between the template signal and the data signal, and
    outputting the quantitative indicator.

8. The method of claim 7, including the additional step of defining the quantitative indicator as either:
    a composite average of coefficients by a calculating step using multiple leads that capture at least the data signal; or
    a bar graph showing percentage of fit.

9. The method of claim 1, further including the step of:
    performing a correlation coefficient calculation to identify a best fit between the template signal and the data signal.

10. The method of claim 1, wherein processing the template signal and data signal includes the steps of:
    selecting a QRS-T segment of a reference ECG signal;
    permitting a user to mark a begin point and an end point of the selected QRS-T segment;
    defining the template signal as being a waveform segment between the marked begin and end points of the selected QRS-T segment;
    acquiring the data signal from multiple leads; and
    processing and displaying the template and data signals such that the template signal is overlaid upon the data signal and any overlapping between the data signal and the template signal is indicated by the first color.

11. The method of claim 1, further including the step of:
    retrieving the template signal from a library of signals stored in a storage device.

12. The method of claim 1, further including the steps:
    assigning the first color to be a first primary color;
    assigning the second color to be a second different primary color; and
    assigning the third color to be a third different primary color.

13. The method of claim 1, further including the steps of:
    assigning the second color to be one primary color;
    assigning the third color to be another different primary color; and
    assigning the first color to be a secondary color which is a color complement to one of the second and third colors.

14. The method of claim 1, further including the steps of:
    assigning the first color to be a first secondary color;
    assigning the second color to be a second different secondary color; and
    assigning the third color to be a third different secondary color.

15. A method for displaying closely proximate cardiac signals comprising the steps of:
    processing a template signal to have a first color when displayed on a display;
    processing a data signal to have a second color when displayed on the display; and
    displaying the processed signals in said first and second colors, wherein a portion of the displayed signals overlap one another and are displayed by the displaying step in a third color to show the degree of alignment therebetween, wherein the first color is different than the second and third color, and wherein the template signal and the data signal each comprise a segment of an electrocardiogram waveform signal,
    wherein the displaying step displays the overlapping portions as including (a) perfect matches between the template signal and the data signal, and (b) not perfect matches of closely-approximating, additional portions in which a degree of alignment between the template signal and the data signal exceeds a predetermined threshold value.

* * * * *